(12) United States Patent
Klinman et al.

(10) Patent No.: US 8,030,285 B2
(45) Date of Patent: *Oct. 4, 2011

(54) OLIGODEOXYNUCLEOTIDE AND ITS USE TO INDUCE AN IMMUNE RESPONSE

(75) Inventors: Dennis Klinman, Potomac, MD (US); Ken Ishii, Rockville, MD (US); Daniela Verthelyi, Potomac, MD (US); James J. Mond, Silver Spring, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 1139 days.

This patent is subject to a terminal disclaimer.

(21) Appl. No.: 11/595,211

(22) Filed: Nov. 9, 2006

(65) Prior Publication Data

US 2007/0202575 A1    Aug. 30, 2007

Related U.S. Application Data

(62) Division of application No. 09/958,713, filed as application No. PCT/US00/09839 on Apr. 12, 2000, now abandoned.

(60) Provisional application No. 60/128,898, filed on Apr. 12, 1999.

(51) Int. Cl.
*A61K 39/00* (2006.01)
*A61K 39/38* (2006.01)
*A61K 45/00* (2006.01)
*A61K 47/00* (2006.01)
*A61K 31/70* (2006.01)
*A61K 9/127* (2006.01)
*A01N 43/04* (2006.01)

(52) U.S. Cl. .............. 514/44 R; 424/184.1; 424/278.1; 424/450

(58) Field of Classification Search ................. None
See application file for complete search history.

(56) References Cited

U.S. PATENT DOCUMENTS

| | | |
|---|---|---|
| 6,194,388 B1 | 2/2001 | Krieg et al. |
| 6,207,646 B1 | 3/2001 | Krieg et al. |
| 6,214,806 B1 | 4/2001 | Krieg et al. |
| 6,218,371 B1 | 4/2001 | Krieg et al. |
| 6,239,116 B1 | 5/2001 | Krieg et al. |
| 6,339,068 B1 | 1/2002 | Krieg et al. |
| 6,406,705 B1 | 6/2002 | Davis et al. |
| 6,423,539 B2 | 7/2002 | Fong et al. |
| 6,428,788 B1 | 8/2002 | Debinski et al. |
| 6,429,199 B1 | 8/2002 | Krieg et al. |
| 6,498,148 B1 | 12/2002 | Raz |
| 6,514,948 B1 | 2/2003 | Raz et al. |
| 6,534,062 B2 | 3/2003 | Raz et al. |
| 6,552,006 B2 | 4/2003 | Raz et al. |
| 6,562,798 B1 | 5/2003 | Schwartz |
| 6,589,940 B1 | 7/2003 | Raz et al. |
| 6,610,661 B1 | 8/2003 | Carson et al. |
| 6,613,751 B2 | 9/2003 | Raz et al. |
| 6,653,292 B1 | 11/2003 | Krieg et al. |
| 6,977,245 B2 * | 12/2005 | Klinman et al. ............ 514/44 R |
| 7,354,909 B2 * | 4/2008 | Klinman et al. ............ 514/44 R |
| 7,517,861 B2 * | 4/2009 | Krieg et al. ................ 514/44 R |
| 7,521,063 B2 * | 4/2009 | Klinman et al. ............ 424/282.1 |
| 7,534,772 B2 * | 5/2009 | Weiner et al. .............. 514/44 R |
| 7,585,847 B2 * | 9/2009 | Bratzler et al. ............. 514/44 R |
| 7,615,227 B2 * | 11/2009 | Klinman et al. ............ 424/198.1 |
| 7,666,674 B2 * | 2/2010 | Klinman et al. ............. 435/375 |
| 7,674,777 B2 * | 3/2010 | Krieg et al. ................ 514/44 R |
| 7,699,801 B2 * | 4/2010 | Haynes et al. ................. 604/57 |
| 7,713,529 B2 * | 5/2010 | Krieg et al. ................ 424/184.1 |
| 7,723,022 B2 * | 5/2010 | Krieg et al. ...................... 435/5 |
| 7,723,500 B2 * | 5/2010 | Krieg et al. ................. 536/23.1 |
| 7,758,876 B2 * | 7/2010 | Klinman et al. ............ 424/278.1 |
| 7,879,810 B2 * | 2/2011 | Krieg et al. ................ 514/44 A |
| 7,892,569 B2 * | 2/2011 | Klinman et al. ............ 424/278.1 |
| 7,919,477 B2 * | 4/2011 | Klinman et al. ............ 514/44 R |
| 7,935,351 B2 * | 5/2011 | Klinman et al. ............ 424/198.1 |
| 2001/0034330 A1 | 10/2001 | Kensil |
| 2001/0036462 A1 | 11/2001 | Fong et al. |
| 2001/0044416 A1 | 11/2001 | McCluskie et al. |
| 2001/0046967 A1 | 11/2001 | Van Nest |
| 2002/0006403 A1 | 1/2002 | Yu et al. |
| 2002/0028784 A1 | 3/2002 | Van Nest |
| 2002/0042383 A1 | 4/2002 | Yew et al. |
| 2002/0042387 A1 | 4/2002 | Raz et al. |
| 2002/0055477 A1 | 5/2002 | Van Nest et al. |
| 2002/0064515 A1 | 5/2002 | Krieg et al. |
| 2002/0065236 A1 | 5/2002 | Yew et al. |

(Continued)

FOREIGN PATENT DOCUMENTS

EP           1 198 249        4/2002

(Continued)

OTHER PUBLICATIONS

U.S. Patent No. 6,008,200, issued Dec. 28, 1999, Withdrawn.

(Continued)

*Primary Examiner* — Nita M Minnifield
(74) *Attorney, Agent, or Firm* — Klarquist Sparkman, LLP

(57) ABSTRACT

The present invention provides a substantially pure or isolated oligodeoxynucleotide of at least about 10 nucleotides comprising a sequence represented by either the formula:

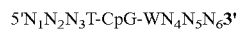

wherein the central CpG motif is unmethylated, W is A or T, and $N_1$, $N_2$, $N_3$, $N_4$, $N_5$, and $N_6$ are any nucleotides, or the formula:

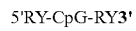

wherein the central CpG motif is unmethylated, R is. A or G, and Y is C or T, as well as an oligodeoxynucleotide delivery complex and a pharmacological composition comprising the present inventive oligodeoxynucleotide, and a method of inducing an immune response by administering the present inventive oligodeoxynucleotide to a host.

32 Claims, No Drawings

U.S. PATENT DOCUMENTS

| | | | |
|---|---|---|---|
| 2002/0086295 | A1 | 7/2002 | Raz et al. |
| 2002/0086839 | A1 | 7/2002 | Raz et al. |
| 2002/0090724 | A1 | 7/2002 | Taylor et al. |
| 2002/0091095 | A1 | 7/2002 | Phillips et al. |
| 2002/0091097 | A1 | 7/2002 | Bratzler et al. |
| 2005/0209184 | A1* | 9/2005 | Klinman et al. ............ 514/44 |
| 2007/0202575 | A1* | 8/2007 | Klinman et al. ............ 435/91.1 |
| 2011/0033421 | A1* | 2/2011 | Hartmann et al. ............ 424/85.7 |
| 2011/0038896 | A1* | 2/2011 | Van Nest et al. ............ 424/400 |

FOREIGN PATENT DOCUMENTS

| | | |
|---|---|---|
| WO | WO 92/18522 | 10/1992 |
| WO | WO 94/19945 | 9/1994 |
| WO | WO 96/02555 A1 * | 2/1996 |
| WO | WO 97/28259 | 8/1997 |
| WO | WO 98/18810 A1 * | 5/1998 |
| WO | WO 98/37919 * | 9/1998 |
| WO | WO 99/11275 | 3/1999 |
| WO | WO 00/06588 | 2/2000 |
| WO | WO 00/20039 | 4/2000 |
| WO | WO 00/21556 | 4/2000 |
| WO | WO 00/61151 | 10/2000 |
| WO | WO 00/62787 | 10/2000 |
| WO | WO 00/67023 | 11/2000 |
| WO | WO 01/00232 | 1/2001 |
| WO | WO 01/02007 | 1/2001 |
| WO | WO 01/12223 | 2/2001 |
| WO | WO 01/22990 | 4/2001 |
| WO | WO 01/51500 | 7/2001 |
| WO | WO 01/55341 | 8/2001 |
| WO | WO 01/68077 | 9/2001 |
| WO | WO 01/68103 | 9/2001 |
| WO | WO 01/68116 | 9/2001 |
| WO | WO 01/68117 | 9/2001 |

OTHER PUBLICATIONS

Anfossi, et al., "An oligomer complementary to c-myb-encoded mRNA inhibits proliferation of human myeloid leukemia cell lines". Proc. Natl, Acad. Sci. USA 86:3379-3383 (1989).

Bauer, et al., "Bacterial CpG-Dna Triggers Activation and Maturation of Human CD11c−, CD123+ Dendritic Cells". J. Immunol. 166:5000-5007 (2001).

Benimetskaya, et al., "Formation of a G-tetrad and higher order structures correlates with biological activity of the RelA (NF-kBp65) 'antisense' oligodeoxynucleotide". Nucleic Acids Research 25(13):2648-2656 (1997).

Boggs, et al., "Characterization and modulation of immune stimulation by modified oligonucleotides". Antisense Nucl. Acid Drug Dev. 7(5):461-471 (1997).

Branda, et al., "Amplification of antibody production by phosphorothioate oligodeoxynucleotides". J. Lab Clin. Med. 128(3):329-338 (1996).

Chu, et al., "CpG oligodeoxynucleotides act as adjuvants that switch on T helper 1 (Th1) immunity". J. Exp. Med. 186(10):1623-1631 (1997).

Deml, et al., "Immunostimulatory CpG motifs trigger a T Helper-1 immune response to Human Immunodeficiency Virus Type-1 (HIV-1) gp160 envelope protein". Clin. Chem. Lab. Med. 37(3):199-204 (1999).

Gao, et al., "Phosphorothioate oligonucleotides are inhibitors of human DNA polymerases and Rnase H: Implications for antisense technology". Mol. Pharmacol. 41:223-229 (1992).

Gursel, et al., "Differential and Competitive Activation of Human Immune Cells by Distinct Classes of CpG Oligodeoxynucleotide". J. Leuko. Biol. 71:813-820 (2002).

Halpern, et al., "Bacterial DNA induces murine interferon-gamma production by stimulation of interleukin-12 and tumor necrosis factor-alpha". Cell Immunol. 167(1):72-78 (1996).

Ishibashi, et al., "Sp1 Decoy Transfected to Carcinoma Cells Suppresses the Expression of Vascular Endothelial Growth Factor, Transforming Growth Factor β, and Tissue Factor and Also Cell Growth and Invasion Activities". Cancer Research 60:6531-6536 (2000).

Iversen, et al., "Pharmacokinetics of an antisense phosphorothioate oigodeoxynucleotide against rev from human immunodeficiency virus type 1 in the adult male rat following single inections and continuous infusion". Antisense Res. Dev. 4:43-52 (1994).

Jilek, et al., "Antigen-Independent Suppression of the Allergic Immune Response to Bee Venom Phospholipase A2 by DNA Vaccination in CBA/J Mice". J. Immunol. 166:3612-3621 (2001).

Kadowaki, et al., "Distinct CpG DNA and Polyinosinic-Polycytidylic Acid Double Stranded RNA, Respectively, Stimulate CD11c− Type 2 Dendritic Cell Precursoes and CD11c+ Dendritic cells to Produce Type I IFN". J. Immunol. 166:2291-2295 (2001).

Klinman, et al., "Activation of the innate immune system by CpG oligodeoxynucleotides: immunoprotective activity and safety". Springer Semin. Immunopathol. 22:173-183 (2000).

Krieg, et al., "CpG motifs in bacterial DNA and their immune effect". Annu. Rev. Immunol. 20:709-760 (2002).

Krieg, et al., "Brief Communication: Oligodeoxynucleotide Modifications Determine the Magnitude of B-Cell Stimulation by CpG Motifs". Antisense & Nucleic Acid Drug Development 6:133-139 (1996).

Krieg, et al., "Leukocyte stimulation by oligodeoxynucleotides". Applied Antisense Oligonucleotide Tech. (BOOK):431-448 (1998).

Krieg, et al., "CpG DNA: A pathogenic factor in systemic lupus erythematosus?". J. Clin. Immunol. 15(6):284-292 (1995).

Krieg, et al., "A role for endogenous retroviral sequences in the regulation of lymphocyte activation". J. Immunol. 143(8):2448-2451 (1989).

Krieg, et al., "CpG motifs in bacterial DNA trigger direct B-cell activation". Nature 374:546-549 (1995).

Krug, et al., "Identification of CpG Oligonucleotide Sequences with High Induction of IFN-α/β in Plasmacytoid Dendritic Cells". Eur. J. Immunol. 31:2154-2163 (2001).

Krug, et al., "Toll-like Receptor Expression Reveals CpG DNA as a Unigue Microbial Stimulus for Plasmacytoid Dendritic Cells Which Synergizes With CD40 Ligand to Induce High Amounts of IL-12". Eur. J. Immunol. 31:3026-3037 (2001).

Kuramoto, et al., "Oligonucleotide sequences required for natural killer cell activation". Jpn. J. Cancer Res. 83:1128-1131 (1992).

Lang, et al., "Guanosine-rich oligodeoxynucleotides induce proliferation of macrophage progenitors in cultures of murine bone marrow cells". Eur. J. Immunol. 29:3496-3506 (1999).

Lapatschek, et al., "Activation of Macrophages and B Lymphocytes by an Oligodeoxynucleotide Derived from an Acutely Pathogenic Simian Immunodeficiency Virus". Antisense Nucleic Acid Drug Dev. 8(5):357-370 (1998).

Maltese, et al., "Sequence context of antisense RelA/NF-kB phohphorothioates determines specificity". Nucleic Acids Research 23(7):1146-1151 (1995).

Manzel, et al., "Lack of Immune Stimulation by Immobilized CpG-oligonucletide". Antisense & Nucleic Acid Drug Development 9(5):459-464 (1999).

Matson, et al., "Nonspecific suppression of [3H]thymidine incorporation by control oligonucleotides". Antisense Res. Dev. 2(4):325-330 (1992).

McIntyre, et al., "A sense phosphorothioate oligonucleotide directed to the initiation codon of transcription factor NF-kappa B p65 causes sequence-specific immune stimulation". Antisense Res. Dev. 3(4):309-322 (1993).

Pisetsky, "Immunological consequences of nucleic acid therapy". Antisense Res. Dev. 5:219-225 (1995).

Prasad, et al., "Oligonucleotides Tethered to a Short Polyguanylic Acid Stretch are Targeted to Macrophages: Enhanced Antiviral Activity of a Vesicular Stomatitis Virus-Specific Antisense Oligonucleotide". Antimicrobial Agents and Chemotherapy 43(11):2689-2696 (Nov. 1999).

Raz, et al., "Intradermal gene immunization: the possible role of DNA uptake in the induction of cellular immunity to viruses". Proc. Natl. Acad. Sci. USA 91:9519-9523 (1994).

Roman, et al., "Immunostimulatory DNA sequences function as T helper-1-promoting aduvants". Nature Med. 3(8):849-854 (1997).

Schwartz, et al., "CpG motifs in bacterial DNA cause inflammation in the lower respiratory tract". J. Clin. Invest. 100(1):68-73 (1997).

Stacey, et al., "Immunostimulatory DNA as an adjuvant in vaccination against *Leishmania major*". Infect. Immun. 67:3719-3726 (1999).

Tokunaga, et al., "A synthetic single-stranded DNA, poly(dG, dC), induces interferon-α/β and -γ, augments natural killer activity and suppresses tumor growth". Jpn. J. Cancer Res. 79:682-686 (1988).

Tokunaga, et al., "Synthetic oligonucleotides with particular base sequences from the cDNA encoding proteins of Mycobacterium bovis BCG induce interferons and activate natural killer cells". Microbiol. Immunol. 36(1):55-66 (1992).

Verthelyi, et al., "Human Peripheral Blood Cells Differentially Recognize and Respond to Two Distinct CpG Motifs". J. Immunol. 166:2372-2377 (2001).

Verthelyi, et al., "CpG Oligodeoxynucleotides as Vaccine Adjuvants in Primates". J. Immunol. 168:1659-1663 (2002).

Weiner, et al., "Immunostimulatory oligodeoxynucleotides containing the CpG motif are effective as immune adjuvants in tumor antigen immunization". Proc. Natl. Acad. Sci. USA 94:10833-10837 (1997).

Yamamoto, et al., "Ability of oligonucleotides with certain palindromes to induce interferon production and augment natural killer cell activity is associated with their base length". Antisense Res. Dev. 4:119-123 (1994).

Yamamoto, "Unique palindromic sequences in synthetic oligonucleotides are required to induce inf and augment INF-mediated natural killer activity". J. Immunol. 148(12):4072-4076 (1992).

Yamamoto, et al., "Synthetic oligonucleotides with certain palindromes stimulate interferon production of human peripheral blood lymphocytes in vitro". Jpn. J. Cancer Res. 85:775-779 (1994).

Yamamoto, et al., "Mode of action of oligonucleotide fraction extracted from Mycobacterium bovis BeG". Kekkaku 69(9):29-32 (1994).

Yamamoto, et al., "Lipofection of synthetic oligodeoxyribonucleotide having a palindromic sequence AACGTT to murine splenocytes enhances interferon production and natural killer activity". Microbiol. Immunol. 38(10):831-836 (1994).

Yaswen, et al., "Effects of Sequence of Thioated Oligonucleotides on Cultured Human Mammary Epithelial Cells". Antisense Research and Development 3:67-77 (1993).

Yi, et al., "IFN-γ promotes IL-6 and IgM secretion in response to CpG motifs in bacterial DNA and oligonucleotides". J. Immunol. 156:558-564 (1996).

Zelphati, et al., "Inhibition of HIV-1 Replication in Cultured Cells with Antisense Oligonucleotides Encapsulated in Immunoliposomes". Antisense Res. Dev. 3:323 (1993).

Decision of Interference No. 105,171, The Regents of California verus University of Iowa, Coley Pharmaceutical Group, Inc. and the United States of America. Jul. 17, 2006.

Flynn et al., "Prevention and Treatment of Cutaneous *Leishmaniasis* in Primates by Using Synthetic Type D/A Oligodeoxynucleotides Epressing CpG Motifs," *Infection and Immunity* 73(8):4948-4954, Aug. 2005.

Mendez et al., "Coinjection with CpG-Containing Immunostimulatory Oligodeoxynucleotides Reduces the Pathogenicity of a Live Vaccine against Cutaneous *Leishmaniasis* but Maintains Its Potency and Durability," *Infection and Immunity* 71(9):5121-5129, Sep. 2003.

Rhee et al., "Vaccination with Heat-killed Leishmania Antigen or Recombinant Leishmanial Protein and CpG Oligodeoxynucleotides Induces Long-Term Memory CD4+ and CD8+ T Cell Responses and Protection Against *Leishmania major* Infection," *J. Experimental Medicine* 195(12):1565-1573 Jun. 17, 2002.

Verthelyi et al., "CpG Oligodeoxynucleotides Protect Normal and SIV-Infected Macaques from *Leishmania* Infection," *J. Immunology* 170:4717-4723, 2003.

Mutwiri et al., "Biological activity of immunostimulatory CpG DNA motifs in domestic animals. *Veterinary Immunology and Immunopathology*," 91:89-103 (2003).

Krieg et al., "CpG motif in bacterial DNA and their immune effects," *Annual Rev. Immunol.* 20:709-760 (2002).

Masihi, K., "Fighting infection using immunomodulatory agents," *Expert Opin. Biol. Ther.* 1(4):641-653 (2001).

* cited by examiner

OLIGODEOXYNUCLEOTIDE AND ITS USE TO INDUCE AN IMMUNE RESPONSE

CROSS REFERENCE TO RELATED APPLICATIONS

This is a divisional of U.S. patent application Ser. No. 09/958,713 filed Oct. 7, 2002, now abandoned, which is a §371 U.S. national stage of International Application No. PCT/US00/09839 filed Apr. 12, 2000, which was published in English under PCT Article 21(2), which in turn claims the benefit of U.S. Provisional Application 60/128,898 filed Apr. 12, 1999. The prior applications are incorporated herein in their entirety.

TECHNICAL FIELD OF THE INVENTION

The present invention relates generally to induction of an immune response using specific oligodeoxynucleotides (ODNs).

BACKGROUND OF THE INVENTION

DNA is a complex macromolecule whose immunological activities are influenced by its base composition and base modification, as well as helical orientation. Certain unusual DNA structures (e.g., Z-DNA) can induce significant antibody responses when administered to normal mice. In addition, bacterial DNA, as well as certain synthetic ODNs containing unmethylated CpG sequences can induce proliferation and immunoglobulin (Ig) production by murine B cells. Unmethylated CpG dinucleotides are more frequent in the genomes of bacteria and viruses than vertebrates. Recent studies suggest that immune recognition of these motifs may contribute to the host's innate immune response. D. M. Klinman et al., *CpG Motifs Present in Bacterial DNA Rapidly Induce Lymphocytes to Secrete Interleukin 6, Interleukin 12, and Interferon γ,* 93 Proc. Natl. Acad. Sci. USA 2879 (1996); A.-K. Yi et al., *Rapid Immune Activation by CpG Motifs' in Bacterial DNA,* 157 J. Immun. 5394 (1996); Hua Liang et al., *Activation of Human B Cells by Phosphorothioate Oligodeoxynucleotides,* 98 J. Clin. Invest. 1119 (1996); A. M. Krieg et al., *CpG Motifs in Bacterial DNA Trigger Direct B-Cell Activation,* 374 Nature 546 (1995).

In mice, CpG DNA induces proliferation in almost all (>95%) of B cells and increases Ig secretion. This B-cell activation by CpG DNA is T-cell independent and antigen non-specific. In addition to its direct effects on B cells, CpG DNA also directly activates monocytes, macrophages, and dendritic cells to secrete a variety of cytokines. These cytokines stimulate natural killer (NK) cells to secrete γ-inteferon (IFN-γ) and have increased lytic activity. Examples of which can be found in International Patent Applications WO 95/26204, WO 96/02555, WO 98/11211, WO 98/18810, WO 98/37919, WO 98/40100, WO 98/52581, PCT/US98/047703, and PCT/US99/07335; U.S. Pat. No. 5,663,153; and U.S. patent application Ser. Nos. 08/276,358, 08/386,063, 08/461,036, 08/462/799, 08/960,774, 08/738,652, 09/030,701, 09/082,649, 09/191,170, 09/09/136,138, 09/154,614, and 09/286,098.

Although bacterial DNA and certain ODNs can induce a murine immune response, little is known about the immunostimulatory capacity of these materials for the human immune system. Z. K. Ballas et al., *Induction of NK Activity in Murine and Human Cells by CpG Motifs in Oligodeoxynucleotides and Bacterial DNA,* 157 J. Immun. 1840 (1996). Differences in the responsiveness of human and murine B cells to certain stimuli render it impossible to extrapolate results obtained from mouse to man.

In view of the above, there exists a need for ODNs that induce an immune response in humans. In addition, there is a need for methods utilizing ODNs in the treatment of human diseases. The present invention provides such ODNs and methods of use. These and other advantages of the present invention, as well as additional inventive features, will be apparent from the description of the invention provided herein.

BRIEF SUMMARY OF THE INVENTION

The present invention provides a substantially pure or isolated ODN of at least about 10 nucleotides comprising a sequence represented by either the formula:

$$5'N_1N_2N_3T\text{-}CpG\text{-}WN_4N_5N_6 3'$$

wherein the central CpG motif is unmethylated, W is A or T, and $N_1$, N7, $N_3$, $N_4$, $N_5$, and $N_6$ are any nucleotides, or the formula:

$$5'RY\text{-}CpG\text{-}RY 3'$$

wherein the central CpG motif is unmethylated, R is A or G, and Y is C or T. The present invention also provides an ODN delivery complex and pharmacological composition comprising the present inventive ODN, as well as a method of inducing an immune response by administering the present inventive ODN to a host.

DETAILED DESCRIPTION OF THE INVENTION

Oligodeoxynucleotide

The present invention provides novel ODNs. These ODNs have at least about 10 nucleotides and comprise a sequence represented by either the formula:

$$5'N_1N_2N_3T\text{-}CpG\text{-}WN_4N_5N_6 3'$$

wherein the central CpG motif is unmethylated, W is A or T, and $N_1$, $N_2$, $N_3$, $N_4$, $N_5$, and $N_6$ are any nucleotides, or the formula:

$$5'RY\text{-}CpG\text{-}RY 3'$$

wherein the central CpG motif is unmethylated, R is A or G, and Y is C or T. For example, the ODN can be selected from the group consisting of SEQ ID NO: 1 through SEQ ID NO: 99.

Preferably, the ODN of the present invention is substantially pure or isolated. "Substantially pure" refers to an ODN that is substantially free of other materials, particularly other nucleic acids, proteins, lipids, carbohydrates, and other materials with which it may be naturally associated, while "isolated" refers to an ODN that is removed from its natural environment or state. Preferably, the ODN of the present invention consists of about 100 nucleotides or less (e.g., about 10-75 nucleotides). More preferably, the ODN consists of about 50 nucleotides or less (e.g., about 10-40 nucleotides). Even more preferably, the ODN consists of about 30 nucleotides or less (e.g., about 10-20 nucleotides). Most preferably the ODN consists of about 12 to about 16 nucleotides.

Any suitable modification can be used in the present invention to render the ODN resistant to degradation in vivo (e.g., via an exo or endonuclease). Preferably, the modification includes a phosphorothioate modification. The phosphorothioate modifications can occur at either termini, e.g., the last two or three 5' and/or 3' nucleotides can be liked with phosphorothioate bonds. The ODN also can be modified to contain a secondary structure (e.g., stem loop structure) such that it is resistant to degradation. Another modification that renders the ODN less susceptible to degradation is the inclusion of nontraditional bases such as inosine and quesine, as well as acetyl-, thio- and similarly modified forms of adenine, cytidine, guanine, thymine, and uridine. Other modified nucleotides include nonionic DNA analogs, such as alkyl or aryl phosphonates (i.e., the charged phosphonate oxygen is replaced with an alkyl or aryl group, as set forth in U.S. Pat. No. 4,469,863), phosphodiesters and alkylphosphotriesters (i.e., the charged oxygen moiety is alkylated, as set forth in U.S. Pat. No. 5,023,243 and European Patent No. 0 092 574). ODNs containing a diol, such as tetraethyleneglycol or hexaethyleneglycol, at either or both termini, have also been shown to be more resistant to degradation.

Preferably, the ODNs inducing a humoral immune response, e.g., 5' $N_1N_2N_3$T-CpG-W$N_4N_5N_6$ 3', contain a phosphate backbone modification, and more preferably, the phosphate backbone modification is a phosphorothioate backbone modification (i.e., one of the non-bridging oxygens is replaced with sulfur, as set forth in International Patent Application WO 95/26204). For the ODNs inducing a cell-mediated immune response and containing a phosphodiester backbone, e.g., 5' RY-CpG-RY 3', the ODN preferably has been modified to prevent degradation.

Oligodeoxynucleotide Delivery Complex

The present inventive oligodeoxynucleotide delivery complex comprises the present inventive ODN and a targeting means. Any suitable targeting means can be used within the context of the present invention.

An ODN can be associated with (e.g., ionically or covalently bound to, or encapsulated within) a targeting means (e.g., a molecule that results in higher affinity binding to a target cell, such as a B cell). A variety of coupling or cross-linking agents can be used to form the delivery complex, such as protein A, carbodiamide, and N-succinimidyl-3-(2-pyridyldithio) propionate (SPDP). Examples of ODN delivery complexes include ODNs associated with a sterol (e.g., cholesterol), a lipid (e.g., a cationic lipid, virosome or liposome), and a target cell specific binding agent (e.g., a ligand recognized by target cell specific receptor). Preferred complexes must be sufficiently stable in vivo to prevent significant uncoupling prior to internalization by the target cell; however, these complexes can be cleavable under appropriate circumstances such that the ODN can be released in a functional form.

Pharmacological Composition

The present inventive pharmacological composition comprises the present inventive ODN and a pharmacologically acceptable carrier. Pharmacologically acceptable carriers (e.g., physiologically or pharmaceutically acceptable carriers) are well known in the art.

The present inventive pharmacological composition facilitates the use of the present inventive ODN, both in vivo and ex vivo. Such a composition can be suitable for delivery of the active ingredient to any suitable host, such as a patient for medical application, and can be manufactured in a manner that is itself known, e.g., by means of conventional mixing, dissolving, granulating, dragee-making, levigating, emulsifying, encapsulating, entrapping or lyophilizing processes.

Pharmacological compositions for use in accordance with the present invention can be formulated in a conventional manner using one or more pharmacologically (e.g., physiologically or pharmaceutically) acceptable carriers comprising excipients, as well as optional auxiliaries that facilitate processing of the active compounds into preparations which can be used pharmaceutically. Proper formulation is dependent upon the route of administration chosen. Thus, for injection, the active ingredient can be formulated in aqueous solutions, preferably in physiologically compatible buffers. For transmucosal administration, penetrants appropriate to the barrier to be permeated are used in the formulation. Such penetrants are generally known in the art. For oral administration, the active ingredient can be combined with carriers suitable for inclusion into tablets, pills, dragees, capsules, liquids, gels, syrups, slurries, suspensions and the like. For administration by inhalation, the active ingredient is conveniently delivered in the form of an aerosol spray presentation from pressurized packs or a nebuliser, with the use of a suitable propellant. The active ingredient can be formulated for parenteral administration by injection, e.g., by bolus injection or continuous infusion. Such compositions can take such forms as suspensions, solutions or emulsions in oily or aqueous vehicles, and can contain formulatory agents such as suspending, stabilizing and/or dispersing agents. Other pharmacological excipients are known in the art.

Method of Inducing an Immune Response

The present inventive method of inducing an immune response comprises administering the present inventive ODN to a host in order to induce an immune response in the host.

Administration of the present inventive ODN can be by any suitable method. For example, the ODN can be administered in vivo or ex vivo. Preferably, the ODN is administered in vivo to a mammal, particularly a human. Optionally, the ODN can be contained within or conjugated with a protein, hydrocarbon or lipid. Once this molecule is administered, the ODN sequence must be exposed on the surface to induce an immune response. The ODN can also be co-administered with a protein, hydrocarbon, or lipid. Co-administration can be such that the ODN is administered before, at substantially the same time as, or after the protein, hydrocarbon, or lipid. Preferably, the ODN is administered at substantially the same time as the protein, hydrocarbon, or lipid.

After administration of the novel ODNs, while not intending to be bound by any particular theory, it is thought that the ODNs initially act on antigen presenting cells (e.g., macrophages and dendritic cells). These cells then release cytokines, which activate natural killer (NK) cells. Either a cell-mediated or humoral immune response then occurs in the host.

The cell-mediated or local immune response is produced by T cells, which are able to detect the presence of invading pathogens through a recognition system referred to as the T-cell antigen receptor. Upon detection of an antigen, T cells direct the release of multiple T-cell cytokines, including IL-2, IL-3, IFN-$\gamma$, TNF-$\beta$, GM-CSF and high levels of TNF-$\alpha$, and chemokines MIP-1$\alpha$, MIP-1$\beta$, and RANTES. IL-2 is a T-cell growth factor that promotes the production of additional T cells sensitive to the particular antigen. This production constitutes a clone of the T cells. The sensitized T cells attach to cells containing the antigen. T cells carry out a variety of regulatory and defense functions and play a central role in immunologic responses. When stimulated to produce a cell-mediated immune response, some T cells respond by acting as killer cells, killing the host's own cells when these cells are infected or cancerous and therefore recognized as foreign. Some T cells respond by stimulating B cells, while other T cells respond by suppressing immune response. Preferably, if a cell-mediated immune response is induced, non-B cells are activated, more preferably, cytokines are produced, and most preferably, IFN-$\gamma$ is produced.

The humoral or systemic immune response depends on the ability of the B cells to recognize specific antigens. The mechanism by which B cells recognize antigens is through specific receptors on the surface of the B cells. When an antigen attaches to the receptor site of a B cell, the B cell is stimulated to divide. The daughter cells become plasma cells that manufacture antibodies complementary to the attached antigen. Each plasma cell produces thousands of antibody molecules per minute, which are released into the bloodstream. Many B cells appear to be regulated by the helper T cells and suppressor T cells and produce various cytokines, e.g., IL-3, IL-4, IL-5, IL-6, IL-9, IL-10, IL-13, GM-CSF and low levels of TNF-α. Helper T cells stimulate B cells to produce antibodies against antigens, while suppressor T cells inhibit antibody production. Some B cells, however, are T-cell independent and require no stimulation by the T cells. Preferably, if a humoral immune response is induced, B cells are activated, more preferably, IL-6 is produced, and most preferably, antibodies are produced.

In addition, induction of one type of immune response may allow for immune regulation because up regulation of one type of immune response may down regulate the other type of immune response. This immune regulation allows for customizing or tailoring of the type of immune response when administering an ODN.

The present inventive method can be used to treat, prevent, or ameliorate any suitable allergic reaction in combination with any suitable anti-allergenic agent. An allergy, in the context of the present invention, refers to an acquired hypersensitivity to a substance (i.e., an allergen). Allergic conditions include eczema, allergic rhinitis or coryza, hay fever, bronchial asthma, uticaria (hives), food allergies, and other atopic conditions. The list of allergens is extensive and includes pollens, insect venoms, animal dander, dust, fungal spores, and drugs (e.g., penicillin). Examples of natural, animal, and plant allergens can be found in International Patent Application WO 98/18810. Preferably, the present inventive method is used to treat allergic asthma. Suitable anti-allergenic agents include those substances given in treatment of the various allergic conditions described above, examples of which can be found in the Physicians' Desk Reference (1998).

The present inventive method can be used to treat any suitable cancer in combination with any suitable anti-cancer agent. Suitable cancers include cancers of the brain, lung (e.g., small cell and non-small cell), ovary, breast, prostate, and colon, as well as carcinomas and sarcomas. Preferably, the present inventive method is used to treat a solid tumor cancer. Suitable anti-cancer agents include those substances given in treatment of the various conditions described above, examples of which can be found in the *Physicians' Desk Reference* (1998).

The present inventive method can be used to improve the efficacy of any suitable vaccine. Suitable vaccines include those directed against Hepatitis A, B, and C, examples of which can be found in the Physicians' Desk Reference (1998), and DNA vaccines directed against HIV and malaria. See generally D. Klinman et al., *CpG Motifs as Immune Adjuvants,* 17 Vaccine 19-(1999); M. J. McCluskie and H. L. Davis, *CpG DNA is a Potent Enhancer of Systemic & Mucosal Immune Response Against Hepatitis B Surface Antigen with Intra-Nasal Administration to Mice,* 161 J. Immun. 4463 (1998).

The present inventive method can be used to treat, prevent, or ameliorate any suitable disease associated with the immune system. Preferred diseases associated with the immune system are autoimmune disorders and immune system deficiencies, e.g., lupus erythematosus, and autoimmune diseases such as rheumatoid arthritis and multiple sclerosis. Immune system deficiencies include those diseases or disorders in which the immune system is not functioning at normal capacity, or in which it would be useful to boost the immune system response.

The present inventive method can be used with any suitable antisense therapy. Suitable antisense agents are those that bind either with DNA or RNA and block their function by inhibiting expression of the sequence to which the antisense agents are bound. See generally H. Lonnberg et al., *Towards Genomic Drug Therapy with Antisense Oligonucleotides,* 28 Ann. Med. 511 (1996); A. Alama et al., *Antisense Oligonucleotides as Therapeutic Agents,* 36 Phannacol. Res. 171 (1997); K. J. Scanlon et al., *Oligonucleotide-Mediated Modulation of Mammalian Gene Expression,* 9 FASEB J. 1288 (1995); R. Oberbauer, *Not Non-Sense but Antisense—Applications of Antisense Oligonucleotides in Different Fields of Medicine,* 109 Wien Klin Wochenschr 40 (1997).

The present inventive method can be used to treat, prevent, or ameliorate any suitable infection in combination with any suitable anti-infectious agent. Examples include francisella, schistosomiasis, tuberculosis, AIDS, malaria, and leishmania. Examples of suitable infectious viruses, bacteria, fungi, and other organisms (e.g., protists) can be found in International Patent Application WO 98/18810. Suitable anti-infectious agents include those substances given in treatment of the various conditions described elsewhere, examples of which can be found in the Physicians' Desk Reference (1998).

The present inventive method can be used to treat, prevent, or ameliorate the symptoms resulting from exposure to a bio-warfare agent. Suitable bio-warfare agents include those naturally occurring biological agents that have been specifically modified in the laboratory. Often, modification of these agents has altered them such that there is no known treatment. Examples include Ebola, Anthrax, and Listeria. In the course of ameliorating the symptoms after exposure, use of the present inventive ODNs may not cure the patient, but rather can extend the patient's life sufficiently such that some other treatment can then be applied.

The present invention is further described in the following examples. These examples are intended only to illustrate the invention and are not intended to limit the scope of the invention in any way.

EXAMPLES

Example 1

The following example demonstrates induction of an immune response by various ODNs. Induction was measured by production of the cytokines IL-6 and TNF-γ, and cell proliferation.

Human peripheral blood mononuclear cells (PBMC) were isolated, as described elsewhere (Z. K. Ballas et al., 85 J. Allergy Clin. Immunol. 453 (1990); Z. K. Ballas and W. Rasmussen, 45 J. Immunol. 1039 (1990); Z. K. Ballas and W. Rasmussen, 150 J. Immunol. 17 (1993)). ODNs were synthesized on a DNA synthesizer (Applied Biosystems Inc., Foster City, Calif.), as described elsewhere (Beacage and Caruthers, *Deoxynucleoside Phosphoramidites—A New Class of Key Intermediates for Deoxypolynucleotide Synthesis,* 22 Tetrahedron Letters 1859 (1981)). In some ODNs, the normal DNA backbone phosphodiesterase linkages were replaced with phosphorothioate linkages, as described elsewhere (Agrawal et al., 94 Proc. Natl. Acad. Sci. USA 2620 (1997); Agrawal 14 TIB TECH 376 (1996)). To reduce degradation of the ODNs, those that did not have an entire phosphorothioate backbone contained phosphorothioate linkages at the 5' and 3' ends. Cells were incubated for approximately 72 hrs with the various ODNs. IL-6 and TNF-γ levels were determined by ELISA using anti-IL-6 and anti-TNF-γ antibodies, as described elsewhere (Maniatis et al., *Molecular Cloning: A Laboratory Manual*, Cold Spring Harbor Laboratory Press, New York, 1989). Cell proliferation was determined by [$^3$H] thymidine incorporation, as described elsewhere Nang et al., 98 J. Clin. Invest. at 1121).

IL-6 levels and cell proliferation are set forth in Table 1: Induction of a Humoral Immune Response In Vitro. These data demonstrate that a sequence containing 5' $N_1N_2N_3T$-CpG-$WN_4N_5N_6$ 3', wherein the central CpG motif is unmethylated, W is A or T, and $N_1$, $N_2$, $N_3$, $N_4$, $N_5$, and $N_6$ are any nucleotides, is desirable to induce a humoral immune response. In addition, maximum induction was observed for ODNs that contained a phosphorothioate backbone. IFN-γ levels and cell proliferation are set forth in Table 2: Induction of a Cell-Mediated Immune Response In Vitro. These data demonstrate that a sequence containing 5' RY-CpG-RY 3', wherein the central CpG motif is unmethylated, R is A or G and Y is C or T, is desirable to induce a cell-mediated immune response. Maximum induction occurred with ODNs containing phosphodiesterase linkages.

TABLE 1

Induction of a Humoral Immune Response In Vitro.

| | IL-6 Levels (ELISA) | Cell Proliferation ($^3$H Thymidine Incorporation) |
|---|---|---|
| SEQ ID NO: 1 | 65 | 52 |
| SEQ ID NO: 2 | 85 | 44 |
| SEQ ID NO: 3 | 54 | 50 |
| SEQ ID NO: 4 | 48 | 61 |
| SEQ ID NO: 5 | 42 | 100 |
| SEQ ID NO: 6 | 55 | 23 |
| SEQ ID NO: 7 | 35 | 69 |
| SEQ ID NO: 8 | 28 | 38 |
| SEQ ID NO: 9 | 41 | 20 |
| SEQ ID NO: 10 | 42 | 16 |
| SEQ ID NO: 11 | 33 | 77 |
| SEQ ID NO: 12 | 25 | 13 |
| SEQ ID NO: 13 | 28 | 13 |
| SEQ ID NO: 14 | 35 | 67 |
| SEQ ID NO: 15 | 28 | 54 |
| SEQ ID NO: 16 | 39 | 50 |
| SEQ ID NO: 17 | 50 | 32 |
| SEQ ID NO: 18 | 26 | 1 |
| SEQ ID NO: 19 | 12 | 2 |
| SEQ ID NO: 20 | 55 | 92 |
| SEQ ID NO: 21 | 53 | 26 |
| SEQ ID NO: 22 | 8 | 2 |
| SEQ ID NO: 23 | 12 | 1 |
| SEQ ID NO: 24 | 14 | 0 |
| SEQ ID NO: 25 | 30 | 42 |
| SEQ ID NO: 26 | 43 | 60 |
| SEQ ID NO: 27 | 17 | 15 |
| SEQ ID NO: 28 | 14 | 0 |
| SEQ ID NO: 29 | 10 | 1 |
| SEQ ID NO: 30 | 28 | 23 |
| SEQ ID NO: 31 | 16 | 17 |

TABLE 2

Induction of a Cell-Mediated Immune Response In Vitro.

| | IFN-γ Levels (ELISA) | Cell Proliferation ($^3$H Thymidine Incorporation) |
|---|---|---|
| SEQ ID NO: 32 | 78 | 1 |
| SEQ ID NO: 33 | 100 | 2 |
| SEQ ID NO: 34 | 73 | 2 |
| SEQ ID NO: 35 | 88 | 4 |
| SEQ ID NO: 36 | 81 | 5 |
| SEQ ID NO: 37 | 45 | 4 |
| SEQ ID NO: 38 | 78 | 0 |
| SEQ ID NO: 39 | 33 | 5 |
| SEQ ID NO: 40 | 68 | 2 |
| SEQ ID NO: 41 | 54 | 2 |
| SEQ ID NO: 42 | 54 | 1 |
| SEQ ID NO: 43 | 74 | 4 |
| SEQ ID NO: 44 | 53 | 4 |
| SEQ ID NO: 45 | 32 | 9 |
| SEQ ID NO: 46 | 24 | 1 |
| SEQ ID NO: 47 | 23 | 8 |
| SEQ ID NO: 48 | 22 | 25 |
| SEQ ID NO: 49 | 34 | 26 |
| SEQ ID NO: 50 | 36 | 8 |
| SEQ ID NO: 51 | 24 | 17 |
| SEQ ID NO: 52 | 21 | 9 |
| SEQ ID NO: 53 | 19 | 2 |
| SEQ ID NO: 54 | 12 | 8 |
| SEQ ID NO: 55 | 15 | 5 |
| SEQ ID NO: 56 | 22 | 6 |
| SEQ ID NO: 57 | 18 | 3 |
| SEQ ID NO: 58 | 18 | 6 |
| SEQ ID NO: 59 | 12 | 21 |
| SEQ ID NO: 60 | 13 | 4 |
| SEQ ID NO: 61 | — | 2 |
| SEQ ID NO: 62 | 12 | 23 |
| SEQ ID NO: 63 | 16 | 1 |
| SEQ ID NO: 64 | 16 | 4 |
| SEQ ID NO: 65 | 19 | 2 |
| SEQ ID NO: 66 | 16 | 4 |
| SEQ ID NO: 67 | 14 | 2 |
| SEQ ID NO: 68 | 13 | 1 |
| SEQ ID NO: 69 | 12 | 2 |
| SEQ ID NO: 70 | 19 | 2 |
| SEQ ID NO: 71 | 13 | 1 |
| SEQ ID NO: 72 | 14 | 46 |
| SEQ ID NO: 73 | — | 4 |
| SEQ ID NO: 74 | 16 | 1 |
| SEQ ID NO: 75 | 24 | 1 |
| SEQ ID NO: 76 | 13 | 1 |
| SEQ ID NO: 77 | 12 | 1 |
| SEQ ID NO: 78 | 13 | 1 |
| SEQ ID NO: 79 | 13 | 1 |
| SEQ ID NO: 80 | 12 | 1 |
| SEQ ID NO: 81 | 14 | 20 |
| SEQ ID NO: 82 | 14 | 43 |
| SEQ ID NO: 83 | 14 | 1 |
| SEQ ID NO: 84 | 12 | 1 |
| SEQ ID NO: 85 | 15 | 2 |
| SEQ ID NO: 86 | 13 | 1 |
| SEQ ID NO: 87 | 12 | 0 |
| SEQ ID NO: 88 | — | 3 |
| SEQ ID NO: 89 | 15 | 1 |
| SEQ ID NO: 90 | 18 | 2 |
| SEQ ID NO: 91 | 13 | 2 |
| SEQ ID NO: 92 | 12 | 1 |
| SEQ ID NO: 93 | 14 | 2 |
| SEQ ID NO: 94 | 14 | 1 |
| SEQ ID NO: 95 | 44 | 3 |
| SEQ ID NO: 96 | 24 | 1 |
| SEQ ID NO: 97 | 21 | 6 |
| SEQ ID NO: 98 | 36 | 38 |
| SEQ ID NO: 99 | 21 | 26 |

The foregoing data demonstrates the induction of an immune response in human cells, as exemplified by PBMC, and as measured by the production of the cytokines IFN-γ and IL-6, and cell proliferation, occurs upon the administration of various ODNs.

Example 2

The following example demonstrates induction of an immune response ex vivo by various ODNs. Induction was measured by production of the cytokine IL-6.

A human B cell line (RPMI 8226) was maintained according to the manufacturers recommendations. ODNs were synthesized as described in Example 1. In some ODNs, the normal DNA phosphodiesterase linkages were replaced with phosphorothioate linkages, as described in Example 1. To reduce degradation of the ODNs, those that did not have an entire phosphorothioate backbone contained phosphorothioate linkages at the ends. The cells were incubated with various ODNs for 14 hrs. IL-6 production was determined by ELISA using anti-IL-6 antibodies, as described in Example 1.

IL-6 levels are set forth in Table 3: Induction of a Humoral Immune Response Ex Vivo. These data confirm that a sequence containing 5' $N_1N_2N_3T\text{-}CpG\text{-}WN_4N_5N_6$ 3', which are linked by phosphorothioate bonds and wherein the central CpG motif is unmethylated, W is A or T, and $N_1$, $N_2$, $N_3$, $N_4$, $N_5$, and $N_6$ are any nucleotides, is desirable to induce a humoral immune response.

TABLE 3

Induction of a Humoral Immune Response Ex Vivo.

|  | IL-6 Levels (ELISA) |
| --- | --- |
| SEQ ID NO: 1 | 100 |
| SEQ ID NO: 2 | 89 |
| SEQ ID NO: 3 | 85 |
| SEQ ID NO: 4 | 82 |
| SEQ ID NO: 5 | 82 |
| SEQ ID NO: 6 | 78 |
| SEQ ID NO: 7 | 78 |
| SEQ ID NO: 8 | 78 |
| SEQ ID NO: 9 | 73 |
| SEQ ID NO: 10 | 65 |
| SEQ ID NO: 11 | 62 |
| SEQ ID NO: 12 | 58 |
| SEQ ID NO: 13 | 57 |
| SEQ ID NO: 14 | 56 |
| SEQ ID NO: 15 | 50 |
| SEQ ID NO: 16 | 48 |
| SEQ ID NO: 17 | 47 |
| SEQ ID NO: 18 | 45 |
| SEQ ID NO: 19 | 40 |
| SEQ ID NO: 20 | 39 |
| SEQ ID NO: 21 | 33 |
| SEQ ID NO: 22 | 25 |
| SEQ ID NO: 23 | 23 |
| SEQ ID NO: 24 | 21 |
| SEQ ID NO: 25 | 18 |
| SEQ ID NO: 26 | 17 |
| SEQ ID NO: 27 | 17 |
| SEQ ID NO: 28 | 16 |
| SEQ ID NO: 29 | 16 |
| SEQ ID NO: 30 | 13 |
| SEQ ID NO: 31 | 13 |

The foregoing data demonstrates the induction of an immune response in human cells, as exemplified by the human B cell line RPMI 8226, and as measured by production of the cytokine IL-6, occurs upon administration of various ODNs.

The following table lists additional ODNs which fall within the scope of the present invention.

TABLE 4

SEQ ID NO: 100
SEQ ID NO: 101
SEQ ID NO: 102
SEQ ID NO: 103
SEQ ID NO: 104
SEQ ID NO: 105
SEQ ID NO: 106
SEQ ID NO: 107
SEQ ID NO: 108
SEQ ID NO: 109
SEQ ID NO: 110
SEQ ID NO: 111
SEQ ID NO: 112
SEQ ID NO: 113
SEQ ID NO: 114
SEQ ID NO: 115
SEQ ID NO: 116
SEQ ID NO: 117
SEQ ID NO: 118
SEQ ID NO: 119
SEQ ID NO: 120
SEQ ID NO: 121
SEQ ID NO: 122
SEQ ID NO: 123
SEQ ID NO: 124
SEQ ID NO: 125
SEQ ID NO: 126
SEQ ID NO: 127
SEQ ID NO: 128
SEQ ID NO: 129
SEQ ID NO: 130
SEQ ID NO: 131
SEQ ID NO: 132
SEQ ID NO: 133
SEQ ID NO: 134
SEQ ID NO: 135
SEQ ID NO: 136
SEQ ID NO: 137
SEQ ID NO: 138
SEQ ID NO: 139
SEQ ID NO: 140
SEQ ID NO: 141
SEQ ID NO: 142
SEQ ID NO: 143

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and it is intended that the invention may be practiced otherwise than as specifically described herein. Accordingly, this invention includes all modifications encompassed within the spirit and scope of the invention as defined by the following claims.

What is claimed is:

1. A substantially pure or isolated oligodeoxynucleotide, wherein the oligodeoxynucleotide comprises the nucleic acid sequence selected from the group consisting of the nucleic acid sequence set forth as SEQ ID NO: 82, SEQ ID NO: 1, SEQ ID NO: 8, SEQ ID NO: 97 and SEQ ID NO: 101, and wherein the oligodeoxynucleotide is 100 nucleotides or less in length.

2. The oligodeoxynucleotide of claim 1, wherein the oligodeoxynucleotide is modified to prevent degradation.

3. The oligodeoxynucleotide of claim 1, wherein the oligodeoxynucleotide has a phosphate backbone modification.

4. The oligodeoxynucleotide of claim 3, wherein the phosphate backbone modification is a phosphorothioate backbone modification.

5. The oligodeoxynucleotide of claim 1, wherein the oligodeoxynucleotide is 20 nucleotides in length.

6. The oligodeoxynucleotide claim 1, wherein the oligodeoxynucleotide is 50 nucleotides or less in length.

7. The oligodeoxynucleotide of claim 1, wherein the oligodeoxynucleotide is 30 nucleotides or less in length.

8. An oligodeoxynucleotide delivery complex comprising the oligodeoxynucleotide of claim 1 and a targeting means.

9. The oligodeoxynucleotide delivery complex of claim 8, wherein the targeting means is selected from the group consisting of cholesterol, virosome, liposome, lipid, and a target cell specific binding agent.

10. A composition comprising the oligodeoxynucleotide of claim 1 and a pharmacologically acceptable carrier.

11. A method of inducing cytokine production by a peripheral blood mononuclear cell, comprising
contacting the peripheral blood mononuclear cell with an effective amount of the oligodeoxynucleotide of claim 1, thereby inducing the production of the cytokine, wherein the cytokine is interleukin (IL)-6 or interferon γ.

12. The method of claim 11, wherein the oligodeoxynucleotide comprises the nucleic acid sequence set forth as SEQ ID NO: 82.

13. The method of claim 11, wherein the oligodeoxynucleotide consists of the nucleic acid sequence set forth as SEQ ID NO: 82.

14. The method of claim 11, wherein the oligodeoxynucleotide is modified to prevent degradation.

15. The method of claim 11, wherein the oligodeoxynucleotide has a phosphate backbone modification.

16. The method of claim 11, wherein the phosphate backbone modification is a phosphorothioate backbone modification.

17. The method of claim 11, wherein the oligodeoxynucleotide is 50 nucleotides or less in length.

18. The oligodeoxynucleotide of claim 1, wherein the oligodeoxynucleotide comprises the nucleic acid sequence set forth as SEQ ID NO: 82.

19. The oligodeoxynucleotide of claim 6, wherein the oligodeoxynucleotide comprises the nucleic acid sequence set forth as SEQ ID NO: 82.

20. The method of claim 11, wherein the oligodeoxynucleotide comprises the nucleic acid sequence set forth as SEQ ID NO: 1, or SEQ ID NO: 8, wherein the peripheral blood mononuclear cell is a B cell, and wherein the cytokine is IL-6.

21. A substantially pure or isolated oligodeoxynucleotide, wherein the oligodeoxynucleotide consists of the nucleic acid sequence set forth as SEQ ID NO: 82, SEQ ID NO: 1, SEQ ID NO: 8, SEQ ID NO:11, SEQ ID NO: 65, SEQ ID NO: 97 or SEQ ID NO: 101.

22. The method of claim 11, wherein the oligodeoxynucleotide consists of the nucleic acid sequence set forth as SEQ ID NO: 82, SEQ ID NO: 1, SEQ ID NO: 8, SEQ ID NO: 97 or SEQ ID NO: 101.

23. The oligodeoxynucleotide of claim 21, wherein the oligodeoxynucleotide is modified to prevent degradation.

24. The oligodeoxynucleotide of claim 21, wherein the oligodeoxynucleotide has a phosphate backbone modification.

25. The oligodeoxynucleotide of claim 24, wherein the phosphate backbone modification is a phosphorothioate backbone modification.

26. An oligodeoxynucleotide delivery complex comprising the oligodeoxynucleotide of claim 21 and a targeting means.

27. The oligodeoxynucleotide delivery complex of claim 26, wherein the targeting means is selected from the group consisting of cholesterol, virosome, liposome, lipid, and a target cell specific binding agent.

28. A composition comprising the oligodeoxynucleotide of claim 21 and a pharmacologically acceptable carrier.

29. A method of inducing cytokine production by a peripheral blood mononuclear cell, comprising
contacting the peripheral blood mononuclear cell with an effective amount of the oligodeoxynucleotide of claim 21, thereby inducing the production of the cytokine, wherein the cytokine is interleukin (IL)-6 or interferon γ.

30. The method of claim 29, wherein the oligodeoxynucleotide is modified to prevent degradation.

31. The method of claim 29, wherein the oligodeoxynucleotide has a phosphate backbone modification.

32. The method of claim 29, wherein the phosphate backbone modification is a phosphorothioate backbone modification.

* * * * *

SEQUENCE LISTING

<160> NUMBER OF SEQ ID NOS: 143

<210> SEQ ID NO 1
<211> LENGTH: 12
<212> TYPE: DNA

```
<213> ORGANISM: Artificial Sequence
<220> FEATURE:
<223> OTHER INFORMATION: Synthetic Oligonucleotide

<400> SEQUENCE: 1
tcgagcgttc tc                                                             12

<210> SEQ ID NO 2
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 2
atcgactctc gagcgttct                                                      19

<210> SEQ ID NO 3
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 3
tcgtcgtttt gtcgttttgc tgtt                                                24

<210> SEQ ID NO 4
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 4
tctcgagcgt tctc                                                           14

<210> SEQ ID NO 5
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 5
tcgactctcg agcgttctc                                                      19

<210> SEQ ID NO 6
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 6
atcgactagc gttcgttctc                                                     20

<210> SEQ ID NO 7
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 7
actctcgagc gttctc                                                         16
```

```
<210> SEQ ID NO 8
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 8
ctctcgagcg ttctc                                                    15

<210> SEQ ID NO 9
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 9
gtcgacgttg ac                                                       12

<210> SEQ ID NO 10
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 10
gtcggcgttg ac                                                       12

<210> SEQ ID NO 11
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 11
cgactctcga gcgttctc                                                 18

<210> SEQ ID NO 12
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 12
gtcgacgctg ac                                                       12

<210> SEQ ID NO 13
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 13
gtcagcgttg ac                                                       12

<210> SEQ ID NO 14
<211> LENGTH: 17
<212> TYPE: DNA
<213> ORGANISM: Artificial Sequence
<220> FEATURE:
<223> OTHER INFORMATION: Synthetic Oligonucleotide
```

-continued

<400> SEQUENCE: 14
gactctcgag cgttctc                                                  17

<210> SEQ ID NO 15
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 15
gtcgtcgatg ac                                                       12

<210> SEQ ID NO 16
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 16
atgcactctc gagcgttctc                                               20

<210> SEQ ID NO 17
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 17
ctcgagcgtt ctc                                                      13

<210> SEQ ID NO 18
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 18
tgcagcgttc tc                                                       12

<210> SEQ ID NO 19
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 19
tttggcgttt tt                                                       12

<210> SEQ ID NO 20
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 20
atcgactctc gagcgttctc                                               20

<210> SEQ ID NO 21
<211> LENGTH: 20
<212> TYPE: DNA

-continued

<213> ORGANISM: Artificial Sequence
<220> FEATURE:
<223> OTHER INFORMATION: Synthetic Oligonucleotide

<400> SEQUENCE: 21
agcgtttctc gatcgacctc                                                   20

<210> SEQ ID NO 22
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 22
ggtgcaccga tgcaggggg                                                    19

<210> SEQ ID NO 23
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 23
gtcgtcgacg acgg                                                         14

<210> SEQ ID NO 24
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 24
gggggcgttg gg                                                           12

<210> SEQ ID NO 25
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 25
atgcactctg cagcgttctc                                                   20

<210> SEQ ID NO 26
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 26
atcgactctc gaggcttctc                                                   20

<210> SEQ ID NO 27
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 27
ggtgcatcga tgcaggg                                                      17

<210> SEQ ID NO 28
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 28
gggtcgtcgt tttgtcgttt cgttg                                  25

<210> SEQ ID NO 29
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 29
aaaggcgtta aa                                                12

<210> SEQ ID NO 30
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 30
cccggcgttc cc                                                12

<210> SEQ ID NO 31
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 31
gtcatcgatg ca                                                12

<210> SEQ ID NO 32
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 32
ggtgcatcga tgcaggggggg                                       20

<210> SEQ ID NO 33
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 33
ggggtcatcg atgaaaaaaa                                        20

<210> SEQ ID NO 34
<211> LENGTH: 20
<212> TYPE: DNA
<213> ORGANISM: Artificial Sequence
<220> FEATURE:
<223> OTHER INFORMATION: Synthetic Oligonucleotide

```
<400> SEQUENCE: 34
ggtgcatcga tgcagggggg                                              20

<210> SEQ ID NO 35
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 35
aaggtcaacg ttgaaaaaaa                                              20

<210> SEQ ID NO 36
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 36
aaggtcatcg atgggggggg                                              20

<210> SEQ ID NO 37
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 37
ggtgcatcga tgcagggggg                                              20

<210> SEQ ID NO 38
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 38
ggtgcatcga tgcagggggg                                              20

<210> SEQ ID NO 39
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 39
ggtgcgtcga cgcagggggg                                              20

<210> SEQ ID NO 40
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 40
ggtgcgtcga tgcagggggg                                              20

<210> SEQ ID NO 41
<211> LENGTH: 20
<212> TYPE: DNA
```

```
<213> ORGANISM: Artificial Sequence
<220> FEATURE:
<223> OTHER INFORMATION: Synthetic Oligonucleotide

<400> SEQUENCE: 41
ggtgcgtcga cgcagggggg                                                    20

<210> SEQ ID NO 42
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 42
ggtgcaccgg tgcagggggg                                                    20

<210> SEQ ID NO 43
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 43
ggtgcatcga tgcagggggg                                                    20

<210> SEQ ID NO 44
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 44
gtcaacgtcg ac                                                            12

<210> SEQ ID NO 45
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 45
gtcggcgtcg ac                                                            12

<210> SEQ ID NO 46
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 46
ggggtcaacg ttgagggggg                                                    19

<210> SEQ ID NO 47
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 47
gtcggcgctg ac                                                            12
```

<210> SEQ ID NO 48
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 48
atgcactctc gaggcttctc                                           20

<210> SEQ ID NO 49
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 49
aatgcatcga tgcaaaa                                              17

<210> SEQ ID NO 50
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 50
gtcagcgtcg ac                                                   12

<210> SEQ ID NO 51
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 51
gtcaacgttg ac                                                   12

<210> SEQ ID NO 52
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 52
tgcatcgatg ca                                                   12

<210> SEQ ID NO 53
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 53
ggtgcatcga tgcaggggg                                            19

<210> SEQ ID NO 54
<211> LENGTH: 12
<212> TYPE: DNA
<213> ORGANISM: Artificial Sequence
<220> FEATURE:
<223> OTHER INFORMATION: Synthetic Oligonucleotide -continued

```
<400> SEQUENCE: 54
gtcgacgtcg ac                                                         12

<210> SEQ ID NO 55
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 55
gtcgacgccg ac                                                         12

<210> SEQ ID NO 56
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 56
cccaacgttc cc                                                         12

<210> SEQ ID NO 57
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 57
gtcaacgctg ac                                                         12

<210> SEQ ID NO 58
<211> LENGTH: 10
<212> TYPE: DNA
<213> ORGANISM: Artificial Sequence
<220> FEATURE:
<223> OTHER INFORMATION: Synthetic Oligonucleotide

<400> SEQUENCE: 58
gagcgttctc                                                            10

<210> SEQ ID NO 59
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 59
gggaacgttg gg                                                         12

<210> SEQ ID NO 60
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 60
gtcagcgctg ac                                                         12

<210> SEQ ID NO 61
<211> LENGTH: 16
<212> TYPE: DNA
```

```
<213> ORGANISM: Artificial Sequence
<220> FEATURE:
<223> OTHER INFORMATION: Synthetic Oligonucleotide

<400> SEQUENCE: 61
gggggaacgt tcgggg                                                   16

<210> SEQ ID NO 62
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 62
gtcggcgccg ac                                                       12

<210> SEQ ID NO 63
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 63
ggggtaacgt tagggg                                                   16

<210> SEQ ID NO 64
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 64
gtcaacgccg ac                                                       12

<210> SEQ ID NO 65
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 65
tgcctcgagg ca                                                       12

<210> SEQ ID NO 66
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 66
tttaacgttt tt                                                       12

<210> SEQ ID NO 67
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 67
aaaaacgtta aa                                                       12
```

<210> SEQ ID NO 68
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 68
gggggaagct tcgggg                                                         16

<210> SEQ ID NO 69
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 69
gtcagcgccg ac                                                             12

<210> SEQ ID NO 70
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 70
cgagcgttct c                                                              11

<210> SEQ ID NO 71
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 71
ggtgcatcga tgcagg                                                         16

<210> SEQ ID NO 72
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 72
ggtgcatcga tgcagggggg                                                     20

<210> SEQ ID NO 73
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 73
ggtgcatcga tgcaggggg                                                      19

<210> SEQ ID NO 74
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 74
ggcgtcgacg ggg                                                          13

<210> SEQ ID NO 75
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 75
ggtgcgtcgt tgcagggggg                                                   19

<210> SEQ ID NO 76
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 76
ggtgcgccga tgcagggggg                                                   19

<210> SEQ ID NO 77
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 77
gggggatcga tcgggg                                                       16

<210> SEQ ID NO 78
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 78
ggggtcgaca ggg                                                          13

<210> SEQ ID NO 79
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 79
ggtgcgtcgg tgcagggggg                                                   19

<210> SEQ ID NO 80
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 80
gggggatgca tcgggg                                                       16

<210> SEQ ID NO 81
<211> LENGTH: 20
<212> TYPE: DNA

```
<213> ORGANISM: Artificial Sequence
<220> FEATURE:
<223> OTHER INFORMATION: Synthetic Oligonucleotide

<400> SEQUENCE: 81
ggtgcgtcga tgcagggggg                                              20

<210> SEQ ID NO 82
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 82
ggtgcgtcga tgcagggggg                                              20

<210> SEQ ID NO 83
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 83
ggtgcgtcga tgcaggggg                                               19

<210> SEQ ID NO 84
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 84
ggtgcctcga ggcaggggg                                               19

<210> SEQ ID NO 85
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 85
gggggctcga gagggg                                                  16

<210> SEQ ID NO 86
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 86
ggggtatcga tagggg                                                  16

<210> SEQ ID NO 87
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 87
ggtgcatcga tgcgagaga                                               19
```

<210> SEQ ID NO 88
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 88
ggtgcatcga cgcagggggg                                               19

<210> SEQ ID NO 89
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 89
ggggtcaacg ttgaggggggg                                              20

<210> SEQ ID NO 90
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 90
ggtgcatgca tgcagggggg                                               20

<210> SEQ ID NO 91
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 91
ggggtcaagc ttgaggggggg                                              20

<210> SEQ ID NO 92
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 92
ggggtaagct tagggg                                                   16

<210> SEQ ID NO 93
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 93
ggtgcatgca tgcaggg                                                  17

<210> SEQ ID NO 94
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 94
ggtgcataaa tgcagggggg                                                   20

<210> SEQ ID NO 95
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 95
aatgcatgca tgcaaaa                                                      17

<210> SEQ ID NO 96
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 96
ggtgcatgca tgcagggggg                                                   20

<210> SEQ ID NO 97
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 97
atcgactctg caggcttctc                                                   20

<210> SEQ ID NO 98
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 98
tcgaggcttc tc                                                           12

<210> SEQ ID NO 99
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 99
atgcactctg caggcttctc                                                   20

<210> SEQ ID NO 100
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 100
tgcaggcttc tc                                                           12

<210> SEQ ID NO 101
<211> LENGTH: 12
<212> TYPE: DNA

<213> ORGANISM: Artificial Sequence
<220> FEATURE:
<223> OTHER INFORMATION: Synthetic Oligonucleotide

<400> SEQUENCE: 101
tcgtttgttc tc    12

<210> SEQ ID NO 102
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 102
acgagggttc tc    12

<210> SEQ ID NO 103
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 103
ttccttcgag ctc    13

<210> SEQ ID NO 104
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 104
tcgatgcttc tc    12

<210> SEQ ID NO 105
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 105
gcgaggcttc tc    12

<210> SEQ ID NO 106
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 106
ccgaggcttc tc    12

<210> SEQ ID NO 107
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 107
tgcaggcttc tc    12

```
<210> SEQ ID NO 108
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 108
tcgttcgttc tc                                                              12

<210> SEQ ID NO 109
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 109
tcgccgcttc tc                                                              12

<210> SEQ ID NO 110
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 110
tcgaatgttc tc                                                              12

<210> SEQ ID NO 111
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 111
tcgagtgttc tc                                                              12

<210> SEQ ID NO 112
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 112
tcgtatgttc tc                                                              12

<210> SEQ ID NO 113
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 113
tcggatgttc tc                                                              12

<210> SEQ ID NO 114
<211> LENGTH: 12
<212> TYPE: DNA
<213> ORGANISM: Artificial Sequence
<220> FEATURE:
<223> OTHER INFORMATION: Synthetic Oligonucleotide
```

```
<400> SEQUENCE: 114
tcgcatgttc tc                                              12

<210> SEQ ID NO 115
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 115
tcgactgttc tc                                              12

<210> SEQ ID NO 116
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 116
tcgcctgttc tc                                              12

<210> SEQ ID NO 117
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 117
tcggctgttc tc                                              12

<210> SEQ ID NO 118
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 118
tcgtctgttc tc                                              12

<210> SEQ ID NO 119
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 119
tcgtgtgttc tc                                              12

<210> SEQ ID NO 120
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 120
tcgcttgttc tc                                              12

<210> SEQ ID NO 121
<211> LENGTH: 12
<212> TYPE: DNA
```

```
<213> ORGANISM: Artificial Sequence
<220> FEATURE:
<223> OTHER INFORMATION: Synthetic Oligonucleotide

<400> SEQUENCE: 121
ttgttcgaac tc                                                          12

<210> SEQ ID NO 122
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 122
ttgttcgctc tc                                                          12

<210> SEQ ID NO 123
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 123
ttgttcgccc tc                                                          12

<210> SEQ ID NO 124
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 124
ttgttcgggc tc                                                          12

<210> SEQ ID NO 125
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 125
ttgttcgttc tc                                                          12

<210> SEQ ID NO 126
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 126
ttgttcgtac tc                                                          12

<210> SEQ ID NO 127
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 127
tcgagttcgc tc                                                          12
```

<210> SEQ ID NO 128
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 128
tcgagttcgt tc                                                              12

<210> SEQ ID NO 129
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 129
tcgagttcga gc                                                              12

<210> SEQ ID NO 130
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 130
ctcgtttgtt ct                                                              12

<210> SEQ ID NO 131
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 131
ttcgtttgtt ct                                                              12

<210> SEQ ID NO 132
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 132
cccgtttgtt ct                                                              12

<210> SEQ ID NO 133
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 133
tcggttgttc tc                                                              12

<210> SEQ ID NO 134
<211> LENGTH: 11
<212> TYPE: DNA
<213> ORGANISM: Artificial Sequence
<220> FEATURE:
<223> OTHER INFORMATION: Synthetic Oligonucleotide

```
<400> SEQUENCE: 134
tgcgcaaggg g                                              11

<210> SEQ ID NO 135
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 135 tcgcccttc tc                                              12

<210> SEQ ID NO 136
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 136
ggtatatcga tataggggg                                      20

<210> SEQ ID NO 137
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 137
ggtggatcga tccaggggg                                      20

<210> SEQ ID NO 138
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 138
ggtccatcga tccaggggg                                      20

<210> SEQ ID NO 139
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 139
ggtggatcga tggaggggg                                      20

<210> SEQ ID NO 140
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 140
agcgctaggg g                                              11

<210> SEQ ID NO 141
<211> LENGTH: 20
<212> TYPE: DNA
```

-continued

```
<213> ORGANISM: Artificial Sequence
<220> FEATURE:
<223> OTHER INFORMATION: Synthetic Oligonucleotide

<400> SEQUENCE: 141
ggtgcatgta tgcagggggg                                              20

<210> SEQ ID NO 142
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 142
ggtgcacgcg tgcagggggg                                              20

<210> SEQ ID NO 143
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 143
cgttctcggg ggg                                                     13
```